United States Patent [19]

Aoki et al.

[11] 4,340,604

[45] Jul. 20, 1982

[54] METHOD FOR INHIBITING THE LOWERING OF IMMUNOLOGICAL FUNCTION AND AGENT THEREFOR

[75] Inventors: Tadao Aoki; Hideo Miyakoshi; Yoshihei Hirasawa, all of Niigata; Yasuo Nishii, Tokyo, all of Japan

[73] Assignee: Chugai Seiyaku Kabushiki Kaisha, Tokyo, Japan

[21] Appl. No.: 176,641

[22] Filed: Aug. 11, 1980

[30] Foreign Application Priority Data

Aug. 10, 1979 [JP] Japan ................................ 54/101210

[51] Int. Cl.$^3$ ........................................... A01N 45/00
[52] U.S. Cl. ................................................... 424/236
[58] Field of Search ......................................... 424/236

[56] References Cited

U.S. PATENT DOCUMENTS 3,741,996 6/1973 DeLuca et al. ................... 260/397.2
4,164,569 8/1979 Ikushima et al. ................... 426/236
4,225,525 9/1980 Baggiolini et al. ............... 260/397.2

*Primary Examiner*—Elbert L. Roberts
*Attorney, Agent, or Firm*—Browdy and Neimark

[57] ABSTRACT

A method for inhibiting the lowering of immunological function of patients who are suffering from serious renal disorder such as chronic renal failure or uremia which comprises administering 1α-hydroxycholecalciferol to the patients is disclosed. An agent useful in the practice of the method is also disclosed.

3 Claims, No Drawings

METHOD FOR INHIBITING THE LOWERING OF IMMUNOLOGICAL FUNCTION AND AGENT THEREFOR

This invention relates to a method for inhibiting the lowering of immunological function of patients under artificial blood dialysis, and an agent therefor.

Artificial dialysis is conventionally applied as an indispensable treatment to patients who have chronic renal failure or uremia, and it is well known that the immunological function of these patients under artificial dialysis is lowered. However, the cause of such phenomenon has not yet been fully understood.

The inventors sought to find the reason for the difference in immunological function in terms of lymphocyte blast transformation between, prior to and after artificial dialysis of many chronic renal failure or uremia patients, and discovered the fact that a certain immunosuppressive substance accumulated in the blood of the patients after artificial dialysis, and, thus, their immunological function lowered remarkably in comparison with that prior to the artificial dialysis.

The molecular weight of the immunosuppressive substance is estimated by a technique using an ultrafiltration membrane, to be about 50,000 or more and was found to be unstable to heat. However, its particular components, other physicochemical properties and particular mechanism of formation thereof are not fully known.

During studies to clarify these points, it was discovered that some patients, occasionally administered 1-α-hydroxycholecalcipherol (referred to as 1α-OH-D$_3$ hereunder) for the purpose of controlling calcium metabolism, the immunological function was not lowered.

The inventors continued their studies based on the fact and finally completed this invention, which relates to a method for inhibiting the lowering of immunological function of patients under artificial blood dialysis and, an agent containing 1α-OH-D$_3$ as an active ingredient for inhibiting the lowering of immunological function.

Thus, according to the present invention, infectious diseases which can easily be caused by loss of immunological function of patients suffering from renal disorder and treated by an artificial dialysis can be prevented.

The compound, 1α-OH-D$_3$ is known and can be prepared, for example, by a method described in U.S. Pat. No. 3,741,996. The compound has been developed as drug preventing or treating of various diseases which are caused by an abnormal calcium metabolism. Therefore, there has been no report showing or suggesting that the compound has activities concerning immunological function.

EXAMPLE 1

Venous blood from healthy adults was anticoagulated with heparin, and blended with the equivalent volume of physiological saline, and the mixture was added to Ficoll-Conray solution. After centrifugation at 400×G for 30 minutes, lymphocytes were isolated from the mixture and washed three times with Hank's balanced salt solution.

The lymphocytes were suspended in a concentration of $1.5 \times 10^6$ cells/ml in RPMI 1640 culture medium which had been supplemented with penicillin G (100 IU/ml), streptomycin (100 μg/ml) and 20% of heat inactivated calf serum.

The cell suspension (100 μl) was placed in a hole of micro test II plate, and a cell division accelerating substance (referred to as mitogen hereunder) and test plasma as well as RPMI 1640 culture medium were added to the suspension to make the total volume of the mixture to 200 μl. The culture plate was incubated in a humidified atmosphere of 95% air and 5% $CO_2$ at 37° C. Twenty-four hours before the completion of the incubation, 0.1 μCi of methyl-H$^3$-thymidine (specific activity 5 Ci/mol) was added to the mixture.

After completion of the incubation, the lymphocites were recovered by filtration with glass fibers, and the amount of isotope incorporated in the cells was counted by a liquid scintillation counter. In the experiments above, phytohemagglutinin (PHA) or Concanavalin A (Con A) was used as T-cell mitogen and staphage lysate (SPL) was used as T- and B-cell mitogen. In case PHA was used, the incubation was effected for 72 hours, on the other hand, 120 hour incubation was made for Con A or SPL.

Patients under artificial dialysis suffering from chronic renal failure and regularly attending hospital, or suffering from uremia and staying in a hospital were divided to two groups, one of 16 patients and the other of 8 patients. The first group was administered 1α-OH-D$_3$ and the other group was not. A sample of the test plasm was taken from each patient prior to or just after the artificial dialysis.

Incidentally, in order to observe the normal increase in DNA synthesis, a blank test omitting addition of the mitogen was run in parallel at 120 hour incubation to determine the amount of the bound methyl-H$^3$-thymidine.

The results of the test are shown in the following Table. The figures in the table represent counts per minute (cpm) as the mean and standard error.

TABLE

| Test Samples | | PHA | SPL | Con A | Without mitogen |
|---|---|---|---|---|---|
| 1α-OH—D$_3$ administered | Before Artificial Dialysis | 23077 ± 6580 | 13947 ± 6353 | 14032 ± 4642 | 189 ± 134 |
| | After Artificial Dialysis | 23026 ± 6101 | 10937 ± 4683 | 12358 ± 4962 | 187 ± 129 |
| 1α-OH—D$_3$ not administered | Before Artificial Dialysis | 20305 ± 5726 | 10522 ± 6415 | 12054 ± 3637 | 115 ± 83 |
| | After Artificial Dialysis | 11238 ± 7412 | 3593 ± 3754 | 5814 ± 4787 | 64 ± 82 |

As shown in the results in the above table, the administration of 1α-OH-D$_3$ remarkably inhibited the lowering of immunological function of patients under artificial dialysis.

According to this invention, 1α-OH-D$_3$ is usually administered in an amount of from 0.25 to 10 μg/day, preferably from 0.5 to 3 μg/day per adult.

The form of agent is not essential in this invention. However, since the dose of 1α-OH-D$_3$ is much smaller than the usual, it is preferred to formulate it into soft capsules for oral administration. Although the amount of the active ingredient incorporated in a minimum dosage form is not critical, the preferred dosage unit in every capsule, pill, tablet, packet of powder or packet of granule is from 0.1 to 3 μg.

EXAMPLE 2

1α-OH-D$_3$ was dissolved in O.D.O. (triglyceride of medium chain fatty acid: manufactured by Nisshin Seiyu Kabushiki Kaisha, Japan) at a concentration of 10 μg/ml. Separately, the capsule skin components listed below were heated and molten, from which soft capsules containing 1 μg of 1α-OH-D$_3$ per each capsule were prepared by a conventional capsule filler.

| Capsule Skin Formulation: | |
|---|---|
| Gelatin | 10 parts by weight |
| Glycerine | 5 |
| Sorbic acid | 0.08 |
| Purified water | 14 |

What is claimed is:

1. A method for inhibiting the lowering of immunological function of patients under artificial blood dialysis which comprises administering 1α-hydroxycholecaliferol to said patient.

2. A method according to claim 1 wherein 1α-hydroxycholecalciferol is administered in an amount of from 0.25 to 10 μg/day per adult.

3. A method according to claim 2 wherein said amount is of from 0.5 to 3 μg/day per adult.

* * * * *